United States Patent
David et al.

(10) Patent No.: US 7,826,889 B2
(45) Date of Patent: *Nov. 2, 2010

(54) RADIOACTIVE EMISSION DETECTOR EQUIPPED WITH A POSITION TRACKING SYSTEM AND UTILIZATION THEREOF WITH MEDICAL SYSTEMS AND IN MEDICAL PROCEDURES

(75) Inventors: Gal Ben David, Mitzpe Adi (IL); Yoel Zilberstien, Haifa (IL); Yoav Kimchy, Haifa (IL); Roni Amrani, Yokneam (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1593 days.

This patent is subject to a terminal disclaimer.

(21) Appl. No.: 09/727,464

(22) Filed: Dec. 4, 2000

(65) Prior Publication Data

US 2005/0055174 A1   Mar. 10, 2005

Related U.S. Application Data

(63) Continuation-in-part of application No. 09/714,164, filed on Nov. 17, 2000, now abandoned, which is a continuation-in-part of application No. 09/641,973, filed on Aug. 21, 2000.

(51) Int. Cl.
 *A61B 6/00* (2006.01)
(52) U.S. Cl. .................. 600/436; 600/3; 600/407; 606/130; 702/152
(58) Field of Classification Search .......... 600/407, 600/410, 411, 413, 414, 415, 417, 420, 431, 600/425–429, 436, 3; 606/130; 702/152, 702/150
See application file for complete search history.

(56) References Cited

U.S. PATENT DOCUMENTS

| | | | |
|---|---|---|---|
| 3,340,866 A | 9/1967 | Nöller | |
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 4,015,592 A | 4/1977 | Bradley-Moore | |

(Continued)

FOREIGN PATENT DOCUMENTS

EP       0543626       5/1993

(Continued)

OTHER PUBLICATIONS

Piperno et al. "Breast Cancer Screening by Impedance Measurements", Frontiers Med. Biol. Engng., 2(2): 11-17, 1990.

(Continued)

*Primary Examiner*—Brian Casler
*Assistant Examiner*—John F Ramirez

(57) ABSTRACT a system for calculating a position of a radioactivity emitting source in a system-of-coordinates, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for calculating the position of the radioactivity emitting source in the system-of-coordinates.

43 Claims, 5 Drawing Sheets

U.S. PATENT DOCUMENTS

| | | | |
|---|---|---|---|
| 4,278,077 A | 7/1981 | Mizumoto | |
| 4,364,377 A | 12/1982 | Smith | |
| 4,521,688 A | 6/1985 | Yin | |
| H0012 H * | 1/1986 | Bennett et al. | 250/363.09 |
| 4,595,014 A | 6/1986 | Barrett et al. | |
| 4,689,041 A | 8/1987 | Corday et al. | |
| 4,689,621 A | 8/1987 | Kleinberg | |
| 4,731,536 A | 3/1988 | Rische et al. | |
| 4,773,430 A | 9/1988 | Porath | |
| 4,828,841 A | 5/1989 | Porter et al. | |
| 4,844,067 A | 7/1989 | Ikada et al. | |
| 4,844,076 A | 7/1989 | Lesho et al. | |
| 4,928,250 A | 5/1990 | Greenberg et al. | |
| 4,929,832 A | 5/1990 | Ledly | |
| 4,951,653 A | 8/1990 | Fry et al. | |
| 4,995,396 A | 2/1991 | Inaba et al. | |
| 5,032,729 A | 7/1991 | Charpak | |
| 5,033,998 A | 7/1991 | Corday et al. | |
| 5,088,492 A | 2/1992 | Takayama et al. | |
| 5,243,988 A | 9/1993 | Sieben et al. | |
| 5,249,124 A | 9/1993 | DeVito | |
| 5,279,607 A | 1/1994 | Schentag et al. | |
| 5,299,253 A | 3/1994 | Wessels | |
| 5,349,190 A | 9/1994 | Hines et al. | |
| 5,386,446 A | 1/1995 | Fujimoto et al. | |
| 5,395,366 A | 3/1995 | D'Andrea | |
| 5,415,181 A | 5/1995 | Hofgrefe et al. | |
| 5,484,384 A | 1/1996 | Fearnot | |
| 5,489,782 A | 2/1996 | Wernikoff | |
| 5,493,595 A | 2/1996 | Schoolman | |
| 5,519,221 A | 5/1996 | Weinberg | |
| 5,572,999 A | 11/1996 | Funda et al. | |
| 5,579,766 A | 12/1996 | Gray | |
| 5,604,531 A | 2/1997 | Iddan et al. | |
| 5,617,858 A | 4/1997 | Taverna et al. | |
| 5,657,759 A | 8/1997 | Essen-Moller | |
| 5,672,877 A | 9/1997 | Liebig et al. | |
| 5,690,691 A | 11/1997 | Chen et al. | |
| 5,694,933 A | 12/1997 | Madden et al. | |
| 5,695,500 A | 12/1997 | Taylor et al. | |
| 5,716,595 A | 2/1998 | Goldenberg | |
| 5,727,554 A | 3/1998 | Kalend et al. | |
| 5,729,129 A | 3/1998 | Acker | |
| 5,784,432 A | 7/1998 | Kurtz et al. | |
| 5,811,814 A | 9/1998 | Leone et al. | |
| 5,821,541 A | 10/1998 | Tümer | |
| 5,833,603 A | 11/1998 | Kovacs et al. | |
| 5,842,977 A | 12/1998 | Lesho et al. | |
| 5,871,013 A * | 2/1999 | Wainer et al. | 600/407 |
| 5,880,475 A | 3/1999 | Oka et al. | |
| 5,891,030 A | 4/1999 | Johnson et al. | |
| 5,900,533 A | 5/1999 | Chou | |
| 5,939,724 A | 8/1999 | Eisen et al. | |
| 5,961,457 A | 10/1999 | Raylman et al. | |
| 5,984,860 A | 11/1999 | Shan | |
| 5,993,378 A | 11/1999 | Lemelson | |
| 6,002,480 A | 12/1999 | Izatt et al. | |
| 6,076,009 A | 6/2000 | Raylman et al. | |
| 6,082,366 A | 7/2000 | Andra et al. | |
| 6,107,102 A | 8/2000 | Ferrari | |
| 6,115,635 A | 9/2000 | Bourgeois | |
| 6,129,670 A | 10/2000 | Burdette et al. | |
| 6,132,372 A | 10/2000 | Essen-Moller | |
| 6,135,955 A | 10/2000 | Madden et al. | |
| 6,147,353 A | 11/2000 | Gagnon et al. | |
| 6,173,201 B1 | 1/2001 | Front | |
| 6,205,347 B1 | 3/2001 | Morgan et al. | |
| 6,236,880 B1 | 5/2001 | Raylman et al. | |
| 6,239,438 B1 | 5/2001 | Schubert | |
| 6,242,743 B1 | 6/2001 | DeVito et al. | |
| 6,246,901 B1 | 6/2001 | Benaron | |
| 6,280,704 B1 | 8/2001 | Schutt et al. | |
| 6,324,418 B1 | 11/2001 | Crowley et al. | |
| 6,339,652 B1 | 1/2002 | Hawkins et al. | |
| 6,346,706 B1 | 2/2002 | Rogers et al. | |
| 6,368,331 B1 | 4/2002 | Front et al. | |
| 6,415,046 B1 | 7/2002 | Kerut, Sr. | |
| 6,420,711 B2 | 7/2002 | Tuemer | |
| 6,426,917 B1 | 7/2002 | Tabanou et al. | |
| 6,429,431 B1 | 8/2002 | Wilk | |
| 6,438,401 B1 | 8/2002 | Cheng et al. | |
| 6,453,199 B1 | 9/2002 | Kobozev | |
| 6,459,925 B1 | 10/2002 | Nields et al. | |
| 6,480,732 B1 | 11/2002 | Tanaka et al. | |
| 6,484,051 B1 | 11/2002 | Daniel | |
| 6,490,476 B1 | 12/2002 | Townsend et al. | |
| 6,510,336 B1 | 1/2003 | Daghighian et al. | |
| 6,516,213 B1 | 2/2003 | Nevo | |
| 6,549,646 B1 | 4/2003 | Yeh et al. | |
| 6,560,354 B1 | 5/2003 | Maurer et al. | |
| 6,567,687 B2 * | 5/2003 | Front et al. | 600/426 |
| 6,587,710 B1 | 7/2003 | Wainer | |
| 6,592,520 B1 | 7/2003 | Peszynski et al. | |
| 6,602,488 B1 | 8/2003 | Daghighian | |
| 6,607,301 B1 | 8/2003 | Glukhovsky et al. | |
| 6,614,453 B1 | 9/2003 | Suri et al. | |
| 6,628,983 B1 | 9/2003 | Gagnon | |
| 6,628,984 B2 * | 9/2003 | Weinberg | 600/436 |
| 6,632,216 B2 | 10/2003 | Houzego et al. | |
| 6,633,658 B1 | 10/2003 | Dabney et al. | |
| 6,638,752 B2 | 10/2003 | Contag et al. | |
| 6,643,538 B1 | 11/2003 | Majewski et al. | |
| 6,662,036 B2 * | 12/2003 | Cosman | 600/411 |
| 6,680,750 B1 | 1/2004 | Tournier et al. | |
| 6,697,660 B1 | 2/2004 | Robinson | |
| 6,728,583 B2 | 4/2004 | Hallett | |
| 6,771,802 B1 | 8/2004 | Patt et al. | |
| 6,963,770 B2 | 11/2005 | Scarantino et al. | |
| 7,043,063 B1 | 5/2006 | Noble et al. | |
| 7,142,634 B2 | 11/2006 | Engler et al. | |
| 7,176,466 B2 | 2/2007 | Rousso et al. | |
| 7,187,790 B2 | 3/2007 | Sabol et al. | |
| 7,468,513 B2 | 12/2008 | Charron et al. | |
| 7,490,085 B2 | 2/2009 | Walker et al. | |
| 2002/0072784 A1 | 6/2002 | Sheppard et al. | |
| 2002/0087101 A1 * | 7/2002 | Barrick et al. | 600/587 |
| 2002/0099295 A1 | 7/2002 | Gil et al. | |
| 2002/0103431 A1 | 8/2002 | Toker et al. | |
| 2002/0148970 A1 | 10/2002 | Wong et al. | |
| 2002/0168317 A1 | 11/2002 | Daighighian et al. | |
| 2002/0183645 A1 | 12/2002 | Nachaliel | |
| 2003/0081716 A1 | 5/2003 | Tumer | |
| 2003/0191430 A1 | 10/2003 | D'Andrea et al. | |
| 2003/0202629 A1 | 10/2003 | Dunham et al. | |
| 2004/0003001 A1 | 1/2004 | Shimura | |
| 2004/0010397 A1 | 1/2004 | Barbour et al. | |
| 2004/0081623 A1 | 4/2004 | Eriksen et al. | |
| 2004/0086437 A1 | 5/2004 | Jackson et al. | |
| 2004/0101176 A1 | 5/2004 | Mendonca et al. | |
| 2004/0153128 A1 | 8/2004 | Suresh et al. | |
| 2004/0171924 A1 | 9/2004 | Mire et al. | |
| 2004/0204646 A1 | 10/2004 | Nagler et al. | |
| 2005/0020915 A1 | 1/2005 | Bellardinelli et al. | |
| 2005/0215889 A1 | 9/2005 | Patterson, II | |
| 2005/0253073 A1 | 11/2005 | Joram et al. | |
| 2005/0266074 A1 | 12/2005 | Zilberstein et al. | |
| 2006/0160157 A1 | 7/2006 | Zuckerman | |
| 2006/0237652 A1 | 10/2006 | Kimchy et al. | |
| 2007/0156047 A1 | 7/2007 | Nagler et al. | |
| 2007/0166277 A1 | 7/2007 | Liu et al. | |
| 2007/0194241 A1 | 8/2007 | Rousso et al. | |
| 2008/0033291 A1 | 2/2008 | Rousso et al. | |
| 2008/0042067 A1 | 2/2008 | Rousso et al. | |
| 2008/0128626 A1 | 6/2008 | Rousso et al. | |

| | | | |
|---|---|---|---|
| 2008/0230705 | A1 | 9/2008 | Rousso et al. |
| 2008/0237482 | A1 | 10/2008 | Shahar et al. |
| 2008/0260228 | A1 | 10/2008 | Dichterman et al. |
| 2008/0260637 | A1 | 10/2008 | Dickman |
| 2008/0277591 | A1 | 11/2008 | Shahar et al. |
| 2009/0078875 | A1 | 3/2009 | Rousso et al. |
| 2009/0152471 | A1 | 6/2009 | Rousso et al. |
| 2009/0190807 | A1 | 7/2009 | Rousso et al. |

FOREIGN PATENT DOCUMENTS

| | | |
|---|---|---|
| EP | 0697193 | 2/1996 |
| EP | 0887661 | 12/1998 |
| GB | 2031142 | 4/1980 |
| JP | 6-109848 | 4/1994 |
| WO | WO 92/00402 | 9/1992 |
| WO | WO 99/30610 | 6/1999 |
| WO | WO 99/39650 | 8/1999 |
| WO | WO 00/10034 | 2/2000 |
| WO | WO 00/22975 | 4/2000 |
| WO | WO 01/89384 | 11/2001 |
| WO | WO 2008/010227 | 1/2008 |

OTHER PUBLICATIONS

Rajshekhar "Continuous Impedence Monitoring During CT-Guided Stereotactic Surgery: Relative Value in Cystic and Solid Lesions", British Journal of Neurosurgery, 6: 439-444, 1992.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflamation", The Lancet, 354: 765-770, 1999.
Mori et al. "Overexpression of Matrix Metalloproteinase-7mRNA in Human Colon Carcinomas", Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Day et al. "Localization of Radioiodinated Rat Fibrogen in Transplanted Rat Tumors", J. Nat. Cancer Inst., 23: 799-812, 1959.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Hassan et al. "A Radiotelemetry Pill for the Measurement of Ionising Radiation Using A Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Zhang et al. "An Innovative High Efficiency and High Resolution Probe for Prostate Imaging", The Journal of Nuclear Medicine, 68: 18, 2000. Abstract.
Final OA dated Jul. 12, 2007.
Invitation to Pay Additional Fees.
Invitation to pay additional fees dated Apr. 18, 2007.
OA dated Sep. 4, 2008.
OA of Jun. 1, 2006.
OA of Aug. 10, 2007.
OA of Jan. 17, 2006.
OA of Jun. 19, 2006.
OA of Dec. 2, 2007.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Apr. 20, 2006 From the US Patent and Trademark Office Re.: U.S. Appl. No. 10/240, 239.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Official Action Dated Jan. 7, 2009 From the US Patent and Trademark Office Re.: U.S. Appl. No. 10/616,307.
Official Action Dated Dec. 16, 2008 From the US Patent and Trademark Office Re.: U.S. Appl. No. 10/343,792.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Nov. 25, 2005 to Office Action of May 13, 2005 From the Patent Office of the People's Republic of China Re.: Application No. 1817689.5.
Response to the International Search Report and the Written Opinion of Oct. 10, 2006 From the International Searching Authority Re.: Application No. PCT/IL06/00059.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Dec. 16, 2008 From the US Patent and Trademark Office Re.: U.S. Appl. No. 10/343,792.
Response Dated Mar. 13, 2008 to Official Action of Dec. 13, 2007 From the US Patent and Trademark Office Re.: U.S. Appl. No. 10/616,301.
Response Dated Mar. 15, 2007 to Official Action of Dec. 15, 2006 From the US Patent and Trademark Office Re.: U.S. Appl. No. 10/616,301.

Response Dated Sep. 22, 2008 to Official Action of Jun. 25, 2008 From US Patent and Trademark Office Re.: U.S. Appl. No. 10/616,301.
Response Dated Oct. 31, 2007 to Official Action of Jul. 12, 2007 From the US Patent and Trademark Office Re.: U.S. Appl. No. 10/616,301.
Response Dated Apr. 7, 2009 to Official Action of Oct. 7, 2008 From the US Patent and Trademark Office Re.: U.S. Appl. No. 10/616,301.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Offical Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Jul. 2, 2007 From the International Searching Authority of the Patent Cooperation Treaty Re.: Application No. PCT/IL2006/001291.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording The Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re.: Application No. 01951883.6.
Appeal Bried Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: Application No. 06832278.3.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568. Suppl. IDS VIII in 25855.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated Mar. 1, 2010 From the US Patent and Trademark Office Re.: U.S. Appl. No. 11/794,799.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Aug. 11, 2009 From the US Patent and Trademark Office Re.: U.S. Appl. No. 09/641,973.
Official Action Dated Mar. 11, 2010 From the US Patent and Trademark Office Re.: U.S. Appl. No. 11/607,075.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Mar. 19, 2010 From the US Patent and Trademark Office Re.: U.S. Appl. No. 10/240,239.
Official Action Dated Sep. 21, 2009 From the US Patent and Trademark Office Re.: U.S. Appl. No. 11/798,017.
Official Action Dated Feb. 23, 2010 From the US Patent and Trademark Office Re.: U.S. Appl. No. 09/641,973.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Oct. 14, 2009 to Official Action of May 14, 2009 From the US Patent and Trademark Office Re.: U.S. Appl. No. 11/656,548.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VS, USA, Nov. 10-16, 2002, XP010663724, 2: 1135-1139, Nov. 10, 2002. p. 1137, First col. 2nd §.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Official Action Dated Apr. 9, 2010 From the US Patent and Trademark Office Re.: U.S. Appl. No. 11/798,017.
Communication Pursuant to Article 94(3) EPC Dated Jul. 22, 2009 From the European Patent Office Re.: Application No. 06809851.6.

Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated Jul. 15, 2009 From the US Patent and Trademark Office Re.: U.S. Appl. No. 10/616,301.
Official Action Dated Jul. 20, 2009 From the US Patent and Trademark Office Re.: U.S. Appl. No. 11/980,617.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Official Action Dated Jan. 7, 2009 From the US Patent and Trademark Office Re.: U.S. Appl. No. 10/616,307.
Summons to Attend Oral Proceedings Pursuant to Rule 115(1) EPC Dated Jan. 16, 2009 From the European Patent Office Re.: Application No. 03810570.6.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
International Search Report dated Sep. 12, 2002 from the International Searching Authority of the Patent Cooperation Treaty Re: Application No. PCT/IL02/00057.
Hayakawa et al. "A PET-MRI Registration Technique for PET Studies of the Rat Brain", Nuclear Medicine & Biology, 27: 121-125, 2000. p. 121, col. 1.
Lavallée et al. "Building a Hybrid Patient's Model for Augmented Reality in Surgery: A Registration Problem", Computing in Biological Medicine, 25(2): 149-164, 1995. p. 149-150.
Kojima et al. "Quantitative Planar Imaging Method for Measurement of Renal Activity by Using a Conjugate-Emission Image and Transmission Data", Medical Physics, 27(3): 608-615, 2000. p. 608.
Pardridge et al. "Tracer Kinetic Model of Blood-Brain Barrier Transport of Plasma Protein-Bound Ligands", Journal of Clinical Investigation, 74: 745-752, 1984.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Huesman et al. "Kinetic Parameter Estimation From SPECT Cone-Beam Projection Measurements", Physics in Medicine and Biology, 43(4): 973-982, 1998.
Reutter et al. "Kinetic Parameter Estimation From Attenuated SPECT Projection Measurements", IEEE Transactions on Nuclear Science, 45 (6): 3007-3013, 1998.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.

* cited by examiner

RADIOACTIVE EMISSION DETECTOR EQUIPPED WITH A POSITION TRACKING SYSTEM AND UTILIZATION THEREOF WITH MEDICAL SYSTEMS AND IN MEDICAL PROCEDURES

This is a continuation-in-part of U.S. patent application Ser. No. 09/714,164, filed Nov. 17, 2000 now abandoned, which is a continuation-in-part of U.S. patent application Ser. No. 09/641,973, filed Aug. 21, 2000.

FIELD AND BACKGROUND OF THE INVENTION

The present invention relates to a radioactive emission detector equipped with a position tracking system. More particularly, the present invention relates to the functional integration of a radioactive emission detector equipped with a position tracking system as above with medical three-dimensional imaging modalities and/or with guided minimal-invasive surgical instruments. The present invention is therefore useful for calculating the position of a concentrated radiopharmaceutical in the body in positional context of imaged portions of the body, which information can be used, for example, for performing an efficient minimally invasive surgical procedure. The present invention further relates to a surgical instrument equipped with a position tracking system and a radioactive emission detector for fine in situ localization during resection and/or biopsy procedures, which surgical instrument is operated in concert with other aspects of the invention.

The use of minimally invasive surgical techniques has dramatically affected the methods and outcomes of surgical procedures. Physically cutting through tissue and organs to visually expose surgical sites in conventional "open surgical" procedures causes tremendous blunt trauma and blood loss. Exposure of internal tissues and organs in this manner also dramatically increases the risk of infection. Trauma, blood loss, and infection all combine to extend recovery times, increase the rate of complications, and require a more intensive care and monitoring regiment. The result of such open surgical procedures is more pain and suffering, higher procedural costs, and greater risk of adverse outcomes.

In contrast, minimally invasive surgical procedures cause little blunt trauma or blood loss and minimize the risk of infection by maintaining the body's natural barriers to infection substantially intact. Minimally invasive surgical procedures result in faster recoveries and cause fewer complications than conventional surgical procedures. Minimally invasive procedures, such as laparoscopic, endoscopic, or cystoscopic surgeries, have replaced more invasive surgical procedures in all areas of surgical medicine. Due to technological advancements in areas such as fiber optics, micro-tool fabrication, imaging and material science, the physician performing the operation has easier-to-operate and more cost effective tools for use in minimally invasive procedures. However, there still exist a host of technical hurdles that limit the efficacy and increase the difficulty of minimally invasive procedures, some of which were overcame by the development of sophisticated imaging techniques. As is further detailed below the present invention offers a yet further advantage in this respect.

U.S. Pat. No. 5,846,513 teaches a system for detecting and destroying living tumor tissue within the body of a living being. The system is arranged to be used with a tumor localizing radiopharmaceutical. The system includes a percutaneously insertable radiation detecting probe, an associated analyzer, and a percutaneously insertable tumor removing instrument, e.g., a resectoscope. The radiation detecting probe includes a needle unit having a radiation sensor component therein and a handle to which the needle unit is releasably mounted. The needle is arranged to be inserted through a small percutaneous portal into the patient's body and is movable to various positions within the suspected tumor to detect the presence of radiation indicative of cancerous tissue. The probe can then be removed and the tumor removing instrument inserted through the portal to destroy and/or remove the cancerous tissue. The instrument not only destroys the tagged tissue, but also removes it from the body of the being so that it can be assayed for radiation to confirm that the removed tissue is cancerous and not healthy tissue. A collimator may be used with the probe to establish the probe's field of view.

The main limitation of this system is that once the body is penetrated, scanning capabilities are limited to a translation movement along the line of penetration.

An effective collimator for gamma radiation must be several mm in thickness and therefore an effective collimator for gamma radiation cannot be engaged with a fine surgical instrument such as a surgical needle. On the other hand, beta radiation is absorbed mainly due to its chemical reactivity after passage of about 0.2-3 mm through biological tissue. Thus, the system described in U.S. Pat. No. 5,846,513 cannot efficiently employ gamma detection because directionality will to a great extent be lost and cannot efficiently employ beta radiation because too high proximity to the radiative source is required, whereas body tissue limits the degree of maneuvering the instrument.

The manipulation of soft tissue organs requires visualization techniques such as computerized tomography (CT), fluoroscopy (X-ray fluoroscopy), magnetic resonance imaging (MRI), optical endoscopy, mammography or ultrasound which distinguish the borders and shapes of soft tissue organs or masses. Over the years, medical imaging has become a vital part in the early detection, diagnosis and treatment of cancer and other diseases. In some cases medical imaging is the first step in preventing the spread of cancer through early detection and in many cases medical imaging makes it possible to cure or eliminate the cancer altogether via subsequent treatment.

An evaluation of the presence or absence of tumor metastasis or invasion has been a major determinant for the achievement of an effective treatment for cancer patients. Studies have determined that about 30% of patients with essentially newly diagnosed tumor will exhibit clinically detectable metastasis. Of the remaining 70% of such patients who are deemed "clinically free" of metastasis, about one-half are curable by local tumor therapy alone. However some of these metastasis or even early stage primary tumors do not show with the imaging tools described above. Moreover often enough the most important part of a tumor to be biopsed or surgically removed is the active, i.e., growing part, whereas using only conventional imaging cannot distinguish this specific part of a tumor from other parts thereof and/or adjacent non affected tissue.

A common practice in order to locate this active part is to mark it with radioactivity tagged materials generally known as radiopharmaceuticals, which are administered orally or intravenously and which tend to concentrate in such areas, as the uptake of such radiopharmaceuticals in the active part of a tumor is higher and more rapid than in the neighboring tumor tissue. Thereafter, a radiation emission detector, typically an invasive detector, is employed for locating the position of the active area.

Medical imaging is often used to build computer models which allow doctors to, for example, guide exact radiation in the treatment of cancer, and to design minimal invasive or open surgical procedures. Moreover, imaging modalities are also used to guide surgeons to the target area inside the patient's body, in the operation room during the surgical procedure. Such procedures may include, for example, biopsies, inserting a localized radiation source for direct treatment of a cancerous lesion, known as brachytherapy (so as to prevent radiation damage to tissues near the lesion), injecting a chemotherapy agent into the cancerous site or removing a cancerous or other lesions.

The aim of all such procedures is to pin-point the target area as precisely as possible in order to get the most precise biopsy results, preferably from the most active part of a tumor, or to remove such a tumor in it's entirety on the one hand with minimal damage to the surrounding, non affected tissues, on the other hand.

However, in the current state of the prior art this goal is yet to be achieved, most of the common imaging modalities such as fluoroscopy, CT, MRI, mammography or ultrasound demonstrate the position and appearance of the entire lesion with anatomical modifications that the lesion causes to it's surrounding tissue, without differentiating between the non-active mass from the physiologically active part thereof.

On the other hand, prior art radiation emission detectors and/or biopsy probes, while being suitable for identifying the location of the radiation site, they leave something to be desired from the standpoint of facilitating the removal or other destruction of the detected cancerous tissue with minimum invasion of the patient.

The combination of modalities, as is offered by the present invention, can reduce the margin of error in positioning such tumors. In addition, the possibility of demonstrating the position of the active part of a tumor superimposed on a scan from an imaging modality that shows the organ or tumor, coupled with the possibility to follow a surgical tool in reference to the afflicted area during a surgical procedure will allow for a more precise and controlled surgical procedures to take place, minimizing the aforementioned problems.

The present invention addresses these and other issues which are further elaborated herein below, and offers the physicians and patients more reliable targeting, that in turn will result in less invasive and less destructive surgical procedures.

SUMMARY OF THE INVENTION

According to one aspect of the present invention there is provided a system for calculating a position of a radioactivity emitting source in a system-of-coordinates, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for calculating the position of the radioactivity emitting source in the system-of-coordinates.

According to another aspect of the present invention there is provided a system for calculating a position of a radioactivity emitting source in a system-of-coordinates, the system comprising (a) at least two radioactive emission detectors; (b) a position tracking system being connected to and/or communicating with the at least radioactive emission detectors; and (c) a data processor being designed and configured for receiving data inputs from the position tracking system and from the at least two radioactive emission detectors and for calculating the position of the radioactivity emitting source in the system-of-coordinates.

According to still another aspect of the present invention there is provided a method for defining a position of a radioactivity emitting source in a system-of-coordinates, the method comprising the steps of (a) providing a radioactive emission detector being connected to or communicating with a position tracking system; and (b) monitoring radioactivity being emitted from the radioactivity emitting source, while at the same time, monitoring the position of the radioactive emission detector in the system-of-coordinates, thereby defining the position of the radioactivity emitting source in the system-of-coordinates.

According to yet another aspect of the present invention there is provided a method for defining a position of a radioactivity emitting source in a system-of-coordinates, the method comprising the steps of (a) providing at least one radioactive emission detector being connected to or communicating with a position tracking system; and (b) monitoring radioactivity being emitted from the radioactivity emitting source, while at the same time, monitoring the position of the at least one radioactive emission detector in the system-of-coordinates, thereby defining the position of the radioactivity emitting source in the system-of-coordinates.

According to yet another aspect of the present invention there is provided a system for calculating a position of a radioactivity emitting source in a first system-of-coordinates and further of projecting the position of the radioactivity emitting source onto a second system-of-coordinates, the system comprising (a) a radioactive emission detector; (b) a position tracking system being connected to and/or communicating with the radioactive emission detector; and (c) a data processor being designed and configured for (i) receiving data inputs from the position tracking system and from the radioactive emission detector; (ii) calculating the position of the radioactivity emitting source in the first system-of-coordinates; and (iii) projecting the position of the radioactivity emitting source onto the second system-of-coordinates.

According to still another aspect of the present invention there is provided a system for calculating a position of a radioactivity emitting source in a first system-of-coordinates and further of projecting the position of the radioactivity emitting source onto a second system-of-coordinates, the system comprising (a) at least two radioactive emission detectors; (b) a position tracking system being connected to and/or communicating with the at least two radioactive emission detectors; and (c) a data processor being designed and configured for (i) receiving data inputs from the position tracking system and from the at least two radioactive emission detectors; (ii) calculating the position of the radioactivity emitting source in the first system-of-coordinates; and (iii) projecting the position of the radioactivity emitting source onto the second system-of-coordinates.

According to still another aspect of the present invention there is provided a method for calculating a position of a radioactivity emitting source in a first system-of-coordinates and for projecting the position of the radioactivity emitting source onto a second system-of-coordinates, the method comprising the steps of (a) providing a radioactive emission detector being connected to or communicating with a position tracking system; and (b) monitoring radioactivity being emitted from the radioactivity emitting source, while at the same time, monitoring the position of the radioactive emission detector in the first system-of-coordinates, thereby defining the position of the radioactivity emitting source in the first system-of-coordinates and projecting the position of the radioactivity emitting source onto the second system-of-coordinates.

According to an additional aspect of the present invention there is provided a method for calculating a position of a radioactivity emitting source in a first system-of-coordinates and for projecting the position of the radioactivity emitting source onto a second system-of-coordinates, the method comprising the steps of (a) providing at least one radioactive emission detector being connected to or communicating with a position tracking system; and (b) monitoring radioactivity being emitted from the radioactivity emitting source, while at the same time, monitoring the position of the at least one radioactive emission detector in the first system-of-coordinates, thereby defining the position of the radioactivity emitting source in the first system-of-coordinates and projecting the position of the radioactivity emitting source onto the second system-of-coordinates.

According to yet an additional aspect of the present invention there is provided a system for calculating a position of a body component and a position of a radiopharmaceutical uptaking portion of the body component within a subject, the system comprising (a) a three-dimensional imaging modality being connected to and/or communicating with a first position tracking system for calculating the position of the body component in a first system-of-coordinates; (b) a radioactive emission detector being connected to and/or communicating with a second position tracking system for tracking a position of the radiopharmaceutical uptaking portion of the body component in a second system-of-coordinates; and (c) at least one data processor being designed and configured for receiving data inputs from the three-dimensional imaging modality, the first position tracking system, the radioactive emission detector and the second position tracking system and calculating the position of the body component and the position of the radiopharmaceutical uptaking portion of the body component in a common system-of-coordinates.

According to yet an additional aspect of the present invention there is provided a method for calculating a position of a body component and a position of a radiopharmaceutical uptaking portion of the body component within a subject, the method comprising the steps of (a) providing a three-dimensional imaging modality being connected to and/or communicating with a first position tracking system and calculating the position of the body component in a first system-of-coordinates; (b) providing a radioactive emission detector being connected to and/or communicating with a second position tracking system and tracking a position of the radiopharmaceutical uptaking portion of the body component in a second system-of-coordinates; and (c) receiving data inputs from the three-dimensional imaging modality, the first position tracking system, the radioactive emission detector and the second position tracking system and calculating the position of the body component and the position of the radiopharmaceutical uptaking portion of the body component in a common system-of-coordinates.

According to still an additional aspect of the present invention there is provided a system for performing an intrabody surgical procedure on a radiopharmaceutical uptaking portion of a body component within a subject, the system comprising (a) a radioactive emission detector being connected to and/or communicating with a first position tracking system for tracking a position of the radiopharmaceutical uptaking portion of the body component in a first system-of-coordinates; (b) a surgical instrument being connected to and/or communicating with a second position tracking system for tracking a position of the surgical instrument in a second system-of-coordinates; and (c) at least one data processor being designed and configured for receiving data inputs from the first position tracking system, the radioactive emission detector and the second position tracking system and for calculating the position of the surgical instrument and the radiopharmaceutical uptaking portion of the body component in a common system-of-coordinates.

According to a further aspect of the present invention there is provided a method for performing an intrabody surgical procedure on a radiopharmaceutical uptaking portion of a body component within a subject, the method comprising the steps of (a) providing a radioactive emission detector being connected to and/or communicating with a first position tracking system and tracking a position of the radiopharmaceutical uptaking portion of the body component in a first system-of-coordinates; (b) providing a surgical instrument being connected to and/or communicating with a second position tracking system and tracking a position of the surgical instrument in a second system-of-coordinates while performing the intrabody surgical procedure; and (c) receiving data inputs from the first position tracking system, the radioactive emission detector and the second position tracking system and calculating the position of the surgical instrument and the radiopharmaceutical uptaking portion of the body component in a common system-of-coordinates while performing the intrabody surgical procedure.

According to further features in preferred embodiments of the invention described below, the second system-of-coordinates serves as the common system-of-coordinates and therefore the position of the radiopharmaceutical uptaking portion of the body component in the first system-of-coordinates is projected onto the second system-of-coordinates.

According to still further features in the described preferred embodiments the first system-of-coordinates serves as the common system-of-coordinates and therefore the position of the surgical instrument in the second system-of-coordinates is projected onto the first system-of-coordinates.

According to still further features in the described preferred embodiments the second system-of-coordinates, the first system-of-coordinates and the common system-of-coordinates are a single system-of-coordinates.

According to still further features in the described preferred embodiments the first system-of-coordinates, the second system-of-coordinates and the common system-of-coordinates are each a separate system-of-coordinates and therefore the position of the surgical instrument in the second system-of-coordinates and the position of the radiopharmaceutical uptaking portion of the body component in the first system-of-coordinates are both projected onto the common system-of-coordinates.

According to still further features in the described preferred embodiments the first position tracking system and the second position tracking system are a single position tracking system.

According to still further features in the described preferred embodiments an image presentation device serves for visual co-presentation of the position of the surgical instrument and the radiopharmaceutical uptaking portion of the body component.

According to still further features in the described preferred embodiments the radioactive emission detector is selected from the group consisting of a narrow beam radioactive emission detector and a spatially sensitive radioactivity detector, such as a gamma camera employed in nuclear imaging.

According to still further features in the described preferred embodiments the first and the second position tracking systems are each individually selected from the group consisting of an articulated arm position tracking system, an accelerometers based position tracking system, a potentiometers based position tracking system, a sound wave based position tracking system, a radiofrequency based position tracking system, an electromagnetic field based position tracking system and an optical based position tracking system.

According to still further features in the described preferred embodiments the surgical instrument is selected from the group consisting of laser probe, cardiac catheter, angioplasty catheter, endoscopic probe, biopsy needle, ultrasonic probe, fiber optic scopes, aspiration tubes, laparoscopy probe, thermal probe and suction/irrigation probe.

According to still further features in the described preferred embodiments the radiopharmaceutical is selected from the group consisting of $^{131}$I, $^{67}$Ga, $^{99M}$Tc methoxyisobutyl isonitrile, $^{201}$TlCl, $^{18}$F-fluorodeoxyglucose, $^{125}$I-fibrinogen and $^{111}$In-octreotide.

According to still further features in the described preferred embodiments the three-dimensional imaging modality is connected to and/or communicating with a third position tracking system and is used for calculating the position of a body component in a third system-of-coordinates.

According to still further features in the described preferred embodiments data inputs are received from the three-dimensional imaging modality and the third position tracking system and are used for calculating the position of the surgical instrument and the position of the radiopharmaceutical uptaking portion of a body component and the position of the body component in a common system-of-coordinates.

According to still further features in the described preferred embodiments the first position tracking system, the second position tracking system and the third position tracking system are a single position tracking system.

According to still further features in the described preferred embodiments the position of the surgical instrument, the radiopharmaceutical uptaking portion of the body component and the body component are co-represented by a visual presentation device.

According to still further features in the described preferred embodiments each of the first, the second and the third position tracking system is independently selected from the group consisting of an articulated arm position tracking system, an accelerometers based position tracking system, a sound wave based position tracking system, a radiofrequency based position tracking system and an electromagnetic field based position tracking system.

According to still further features in the described preferred embodiments the second system-of-coordinates serves as the common system-of-coordinates and therefore the position of the radiopharmaceutical uptaking portion of the body component in the first system-of-coordinates and the position of the body component in the third system-of-coordinates are projected onto the second system-of-coordinates.

According to still further features in the described preferred embodiments the first system-of-coordinates serves as the common system-of-coordinates and therefore the position of the surgical instrument in the second system-of-coordinates and the position of the body component in the third system-of-coordinates are projected onto the first system-of-coordinates.

According to still further features in the described preferred embodiments the third system-of-coordinates serves as the common system-of-coordinates and therefore the position of the surgical instrument in the second system-of-coordinates and the position of the radiopharmaceutical uptaking portion of the body component in the first system-of-coordinates are projected onto the third system-of-coordinates.

According to still further features in the described preferred embodiments the second system-of-coordinates, the first system-of-coordinates, the third system-of-coordinates and the common system-of-coordinates are a single system-of-coordinates.

According to still further features in the described preferred embodiments the second system-of-coordinates, the first system-of-coordinates, the third system-of-coordinates and the common system-of-coordinates are each a separate system-of-coordinates and therefore the position of the surgical instrument in the second system-of-coordinates and the position of the radiopharmaceutical uptaking portion of the body component in the first system-of-coordinates and the position of the body component in the third system-of-coordinates are all projected onto the common system-of-coordinates.

According to another aspect of the present invention there is provided a system for generating a two or three dimensional image of a radioactivity emitting source in a body, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for generating the two or three dimensional image of the radioactivity emitting source.

According to still another aspect of the present invention there is provided a method of generating a two or three dimensional image of a radioactivity emitting source in a body, the system comprising (a) scanning the body with a radioactive emission detector; (b) using a position tracking system being connected to and/or communicating with the radioactive emission detector for determining a position in a three dimensional system of coordinates of the radioactive emission detector; and (c) data processing inputs from the position tracking system and from the radioactive emission detector for generating the two or three dimensional image of the radioactivity emitting source.

According to still another aspect of the present invention there is provided a system for performing an intrabody surgical procedure on a radiopharmaceutical uptaking portion of a body component within a subject, the system comprising a surgical instrument being connected to and/or communicating with a position tracking system for tracking a position of the surgical instrument in a system-of-coordinates, the surgical instrument including a radioactive emission detector coupled thereto for monitoring the radiopharmaceutical in situ. Preferably, radioactive emission detector is sensitive to beta radiation and/or positron radiation. The surgical instrument preferably includes a tissue resecting mechanism and/or a tissue sampling mechanism, such as an aspiration mechanism.

According to an additional aspect of the present invention there is provided a system for calculating a position of a radioactivity emitting source in a system-of-coordinates, the system comprising (a) a surgical instrument designed and constructed for invasing a body of a subject, the surgical instrument including a radioactive emission detector connected thereto or integrated therein; (b) a position tracking system being connected to and/or communicating with the surgical instrument; and (c) a data processor being designed and configured for receiving data inputs from the position tracking system and from the radioactive emission detector and for calculating the position of the radioactivity emitting source in the system-of-coordinates.

According to yet an additional aspect of the present invention there is provided a system for calculating a position of a radioactivity emitting source in a first system-of-coordinates and further for projecting the position of the radioactivity emitting source onto a second system-of-coordinates, the system comprising (a) a surgical instrument designed and constructed for invasing a body of a subject, the surgical instrument including a radioactive emission detector connected thereto or integrated therein; (b) a position tracking system being connected to and/or communicating with the surgical instrument; and (c) a data processor being designed and configured for (i) receiving data inputs from the position tracking system and from the radioactive emission detector; (ii) calculating the position of the radioactivity emitting source in the first system-of-coordinates; (iii) calculating the position of the surgical instrument in the first system-of-coordinates; and (iii) projecting the position of the radioactivity emitting source and of the surgical instrument onto the second system-of-coordinates.

According to still an additional aspect of the present invention there is provided a method for calculating a position of a radioactivity emitting source in a first system-of-coordinates and for projecting the position of the radioactivity emitting source onto a second system-of-coordinates, the method comprising the steps of (a) providing a surgical instrument designed and constructed for invasing a body of a subject, the surgical instrument including a radioactive emission detector connected thereto or integrated therein, the surgical instrument being connected to or communicating with a position tracking system; and (b) monitoring radioactivity being emitted from the radioactivity emitting source, while at the same time, monitoring the position of the radioactive emission detector in the first system-of-coordinates, thereby defining the positions of the radioactivity emitting source and of the surgical instrument in the first system-of-coordinates and projecting the position of the radioactivity emitting source onto the second system-of-coordinates.

According to a further aspect of the present invention there is provided a system for calculating a position of a body component and a position of a radiopharmaceutical uptaking portion of the body component within a subject, the system comprising (a) a three-dimensional imaging modality being connected to and/or communicating with a first position tracking system for calculating the position of the body component in a first system-of-coordinates; (b) a surgical instrument designed and constructed for invasing the body, the surgical instrument including a radioactive emission detector connected thereto or integrated therein, the surgical instrument being connected to and/or communicating with a second position tracking system for tracking a position of the radiopharmaceutical uptaking portion of the body component in a second system-of-coordinates; and (c) at least one data processor being designed and configured for receiving data inputs from the three-dimensional imaging modality, the first position tracking system, the radioactive emission detector and the second position tracking system and calculating the position of the body component, the position of the radiopharmaceutical uptaking portion of the body component and the position of the surgical instrument in a common system-of-coordinates.

According to yet a further aspect of the present invention there is provided a method for calculating a position of a body component and a position of a radiopharmaceutical uptaking portion of the body component within a subject, the method comprising the steps of (a) providing a three-dimensional imaging modality being connected to and/or communicating with a first position tracking system and calculating the position of the body component in a first system-of-coordinates; (b) providing a surgical instrument designed and constructed for invasing the body, the surgical instrument including a radioactive emission detector connected thereto or integrated therein, the surgical instrument being connected to and/or communicating with a second position tracking system for tracking a position of the radiopharmaceutical uptaking portion of the body component in a second system-of-coordinates; and (c) receiving data inputs from the three-dimensional imaging modality, the first position tracking system, the radioactive emission detector and the second position tracking system and calculating the position of the body component, the position of the surgical instrument and the position of the radiopharmaceutical uptaking portion of the body component in a common system-of-coordinates.

The present invention successfully addresses the shortcomings of the presently known configurations by providing a radioactive emission detector per se and/or integrated in a surgical instrument connected to or communicating with a position tracking system and the use thereof in a variety of systems and methods used for medical imaging and/or medical procedures.

Implementation of the methods and systems of the present invention involves performing or completing selected tasks or steps manually, automatically, or a combination thereof. Moreover, according to actual instrumentation and equipment of preferred embodiments of the methods and systems of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable algorithms. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
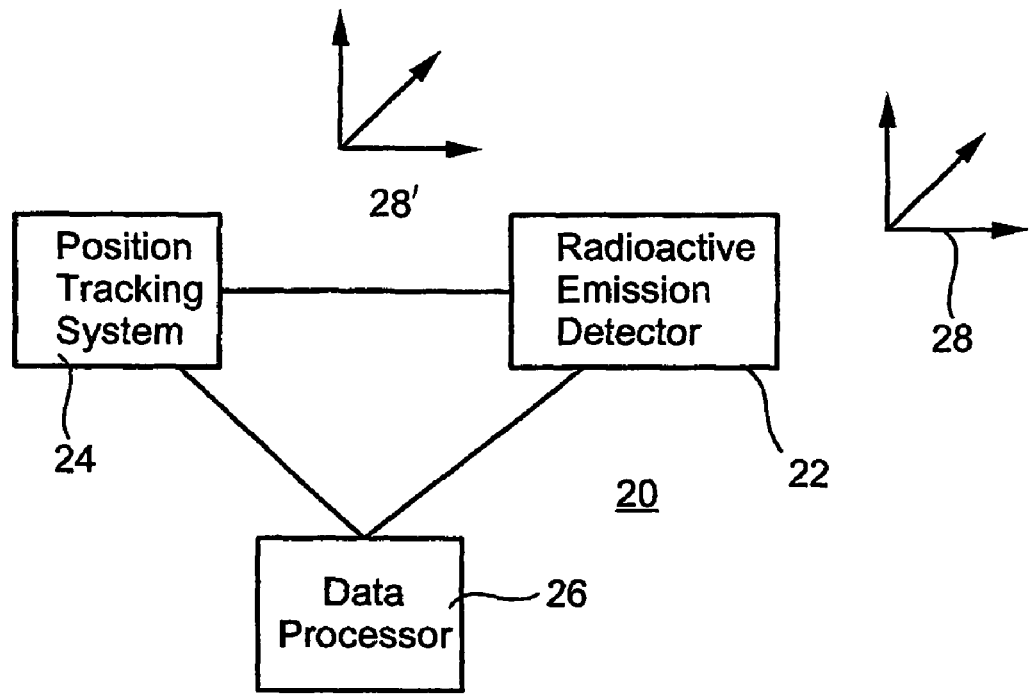
FIG. 1 is a black box diagram of a system according to the teachings of the present invention.

The present invention is of a radioactive emission detector equipped with a position tracking system which can be functionally integrated with medical three-dimensional imaging modalities and/or with guided minimal-invasive or other surgical tools. The present invention can be used for calculating the position of a concentrated radiopharmaceutical in the body in positional context of imaged portions of the body, which information can be used, for example, for performing an efficient and highly accurate minimally invasive surgical procedure.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The use of radioactive materials to tag physiologically active tissue within the body of a patient for determining the tissue's localization and demarcation by radioactive emission detectors has been disclosed in the medical literature for at least forty years. Significant developments in the localization and demarcation of tissue bearing radioactive isotope tags for diagnostic and/or therapeutic purposes have occurred since that time. In fact, it is now becoming an established practice in the diagnosis and/or treatment of certain diseases, e.g., cancer, blood clots and abscesses, to introduce monoclonal antibodies or other agents, e.g., fibrinogen, fluorodeoxyglucose tagged with a radioactive isotope (e.g., $^{99m}$Technetium, $^{67}$Gallium, $^{201}$Thallium, $^{111}$Indium, $^{123}$Iodine, $^{18}$Fluor and $^{125}$Iodine) into the body of the patient. Such radiopharmaceuticals tend to localize in particular tissue, whereas uptake or binding of the specific radiopharmaceutical is increased in more "physiologically active" tissue such as the active core of a cancerous tissue, so that the radiation emitted following nuclear disintegrations of the isotope can be detected by a radiation detector to better allocate the active portion of a tumor. Such radiation may be, for example, $\alpha$, $\beta^-$, $\beta^+$ and/or $\gamma$ radiation.

In another type of applications radioactive substances are used to determine the level of flow of blood in blood vessels and the level of perfusion thereof into a tissue, e.g., coronary flow and myocardial perfusion.

Referring now to the drawings, FIG. 1 illustrates a system for calculating a position of a radioactivity emitting source in a system-of-coordinates, in accordance with the teachings of the present invention, which system is referred to hereinbelow as system 20.

Figure 10:
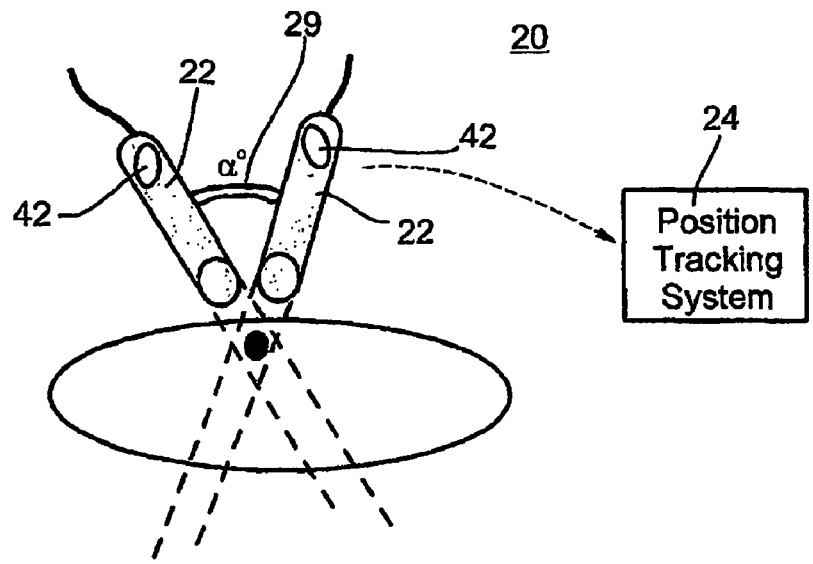
FIG. 10 demonstrates the use of a pair of radiation emission detectors connected therebetween via a connector, preferably a flexible connector or a flexible connection to the connector according to the present invention.

System 20 includes a radioactivity emission detector 22. System 20 according to the present invention further includes a position tracking system 24. System 24 is connected to and/or communicating with radioactive emission detector 22 so as to monitor the position of detector 22 in a three-dimensional space defined by a system-of-coordinates 28 in three or more, say four, five or six degrees-of-freedom. System 20 further includes a data processor 26. Data processor 26 is designed and configured for receiving data inputs from position tracking system 24 and from radioactive emission detector 22 and, as is further detailed below, for calculating the position of the radioactivity emitting source in system-of-coordinates 28. The phrases "system-of-coordinates" and "three-dimensional space" are used herein interchangeably. As shown in FIG. 10, a pair (or more) of detectors 22 connected therebetween via a physical connector, each of detectors 22 is position tracked, can be used for calculating the position of the radioactivity emitting source in system-of-coordinates 28. If more than a single detector 22 is used, detectors 22 are preferably connected therebetween via a connector 29. Connector 29 is preferably flexible. In the alternative, the connections of detectors 22 to connector 29 provide the required flexibility.

Position tracking systems per se are well known in the art and may use any one of a plurality of approaches for the determination of position in a three-dimensional space as is defined by a system-of-coordinates in three and up to six degrees-of-freedom. Some position tracking systems employ movable physical connections and appropriate movement monitoring devices to keep track of positional changes. Thus, such systems, once zeroed, keep track of position changes to thereby determine actual positions at all times. One example for such a position tracking system is an articulated arm.

Figure 2:
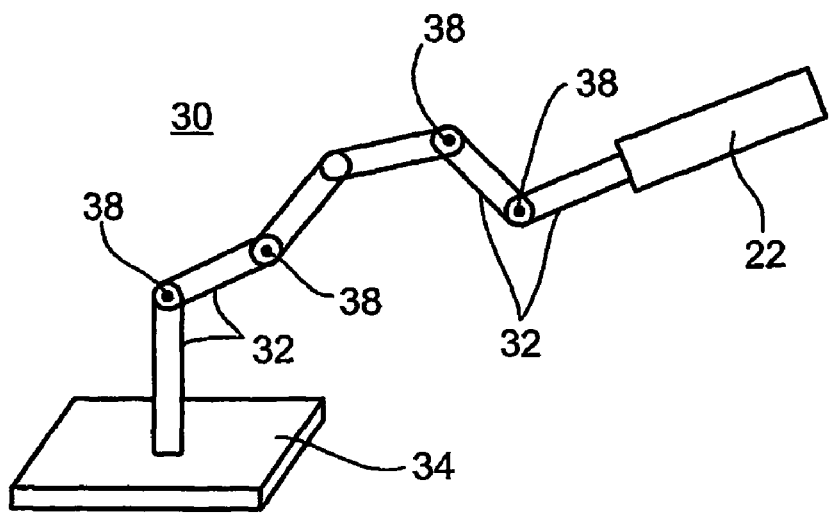
FIG. 2 is a perspective view of an articulated arm which serves as a position tracking system shown carrying a radioactive emission detector in accordance with the teachings of the present invention.

FIG. 2 shows an articulated arm 30 which includes six arm members 32 and a base 34, which can therefore provide positional data in six degrees-of-freedom. Monitoring positional changes may be effected in any one of several different ways. For example, providing each arm member 32 with, e.g., potentiometers 38 used to monitor the angle between adjacent arm members 32 to thereby monitor the angular change of each such arm member with respect to another, so as to determine the position in space of radioactive emission detector 22, which is physically connected to articulated arm 30.

Figure 3:
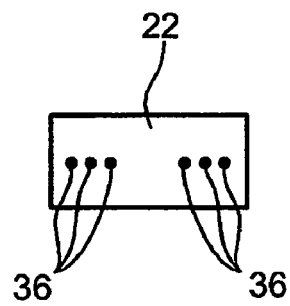
FIG. 3 is a schematic depiction of a radioactive emission detector carrying a pair of three coaxialy aligned accelerometers which serve as a position tracking system in accordance with the teachings of the present invention.

As is shown in FIG. 3 other position tracking systems can be attached directly to radioactive emission detector 22 in order to monitor it's position in space. An example of such a position tracking system is an assortment of three triaxialy (e.g., co-orthogonally) oriented accelerometers 36 which may be used to monitor the positional changes of radioactive emission detector 22 with respect to a space. A pair of such assortments, as is specifically shown in FIG. 3, can be used to determine the position of detector 22 in six-degrees of freedom.

Figure 4:
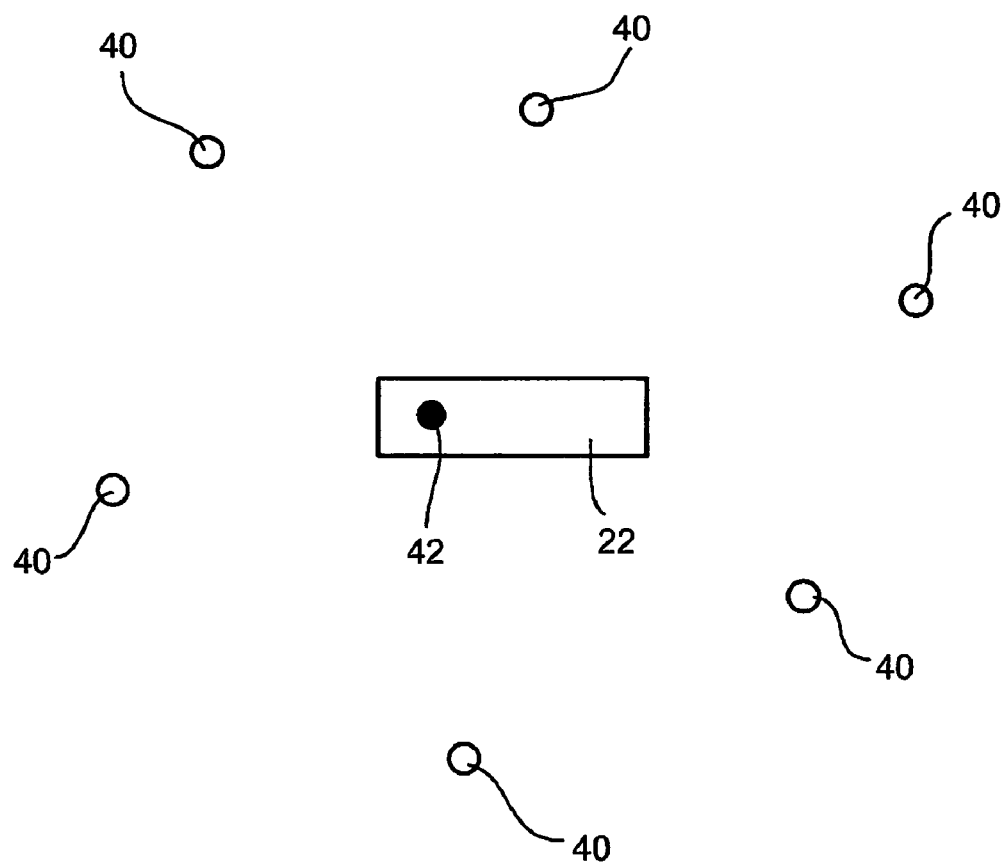
FIG. 4 is a schematic presentation of a radioactive emission detector communicating with yet another type of a position tracking system in accordance with the teachings of the present invention.

As is shown in FIGS. 4 and 10, other position tracking systems re-determine a position irrespective of previous positions, to keep track of positional changes. Such systems typically employ an array of receivers/transmitters 40 which are spread in known positions in a three-dimensional space and transmitter(s)/receiver(s) 42, respectively, which are in physical connection with the object whose position being monitored. Time based triangulation and/or phase shift triangulation are used in such cases to periodically determine the position of the monitored object, radioactive emission detector 22 in this case. Examples of such a position tracking systems employed in a variety of contexts using acoustic (e.g., ultrasound) electromagnetic radiation (e.g., infrared, radiofrequency) or electromagnetic fields are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which are incorporated by reference as if fully set forth herein.

Radioactive emission detectors are well known in the art and may use any one of a number of approaches for the determination of the amount of radioactive emission emanating from an object or portion thereof. Depending on the type of radiation, such detectors typically include substances which when interacting with radioactive decay emitted particles emit either electrons or photons in a level which is proportional over a wide linear range of operation to the level of radiation impinging thereon. The emission of electrons or photons is measurable and therefore serve to quantitatively determine radiation levels. Solid state radioactive emission detectors include CdZnTe detectors, CdTe detectors, HgI detectors, Si detectors, Ge detectors. etc. Scintillation detectors include NaI(Tl) detectors, GSO detectors, CsI detectors, CaF detectors, etc. Also known are gas detectors and scintillation fiber detectors.

Figure 5:
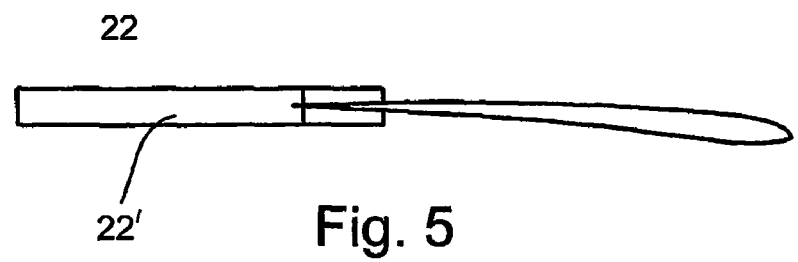
FIG. 5 is a simplified cross-sectional view of a narrow beam radioactive emission detector used to implement an embodiment of the present invention.

FIG. 5 shows a narrow beam radioactive emission detector 22'. Narrow beam radioactive emission detector 22' includes a narrow slit (collimator) so as to allow only radiation arriving from a predetermined angular direction (e.g., 1°-80°) to enter the detector. Narrow beam radioactive emission detectors especially suitable for the configuration shown in FIG. 10 are manufactured by Neoprobe, Dublin, Ohio (www.neoprobe.com), USA, Nuclear Fields, USA (www.nufi.com) Intra-Medical Imaging, Los Angeles, Calif., USA (www.gammaprobe.com).

Figure 6:
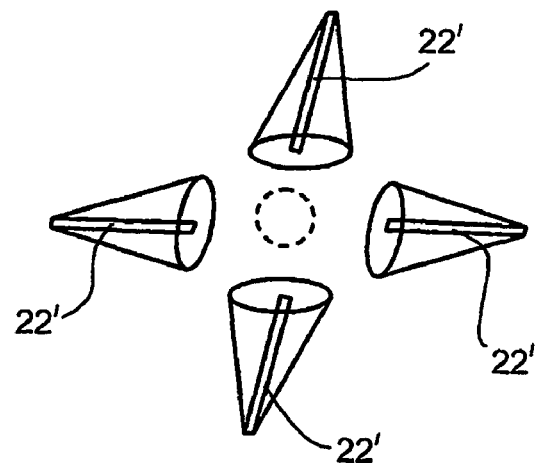
FIG. 6 is a presentation of a scanning protocol which can be effected with the detector of FIG. 5.

As is shown in FIG. 6, such a detector is typically used to measure radioactivity, point by point, by scanning over the surface of a radioactive object from a plurality of directions and distances. In the example shown one scans from four different directions are employed. It will be appreciated that if sufficient radioactivity records are collected from different angles and distances, and the orientation and position in space of detector 22' is simultaneously monitored and recorded during such scans, a three-dimensional model of a radioactive region can be reconstituted and its position in space determined. If two or more detectors are co-employed, as shown in the configuration of FIG. 10, the results may be collected faster.

Figure 7:
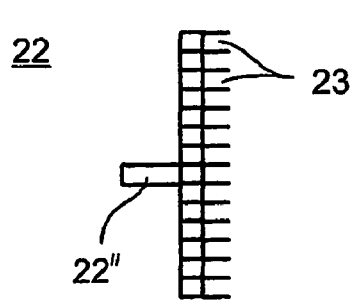
FIG. 7 is a simplified cross-sectional view of a spatially sensitive radioactive emission detector, e.g., a gamma camera, used to implement another embodiment of the present invention.
Figure 8:
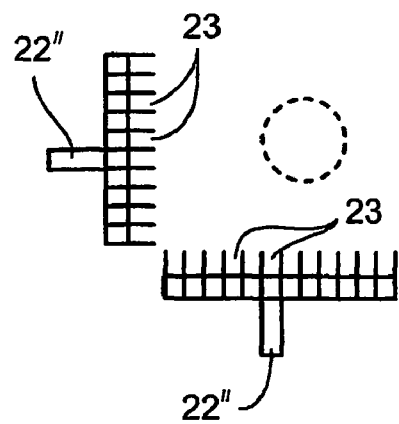
FIG. 8 is a presentation of a scanning protocol which can be effected with the detector of FIG. 7.

FIG. 7 shows another example of a radioactive emission detector, a spatially sensitive radioactive emission detector 22" (such as a gamma camera). Detector 22", in effect, includes an array of multitude narrow beam detector units 23. Such an arrangement is used in accordance with the teachings of the present invention to reduce the amount of measurements and angles necessary to acquire sufficient data so as to reconstitute a three-dimensional model of the radioactive object. Examples of spatially sensitive radioactive emission detectors employed in a variety of contexts are disclosed in, for example, U.S. Pat. Nos. 4,019,057; 4,550,250; 4,831,262; and 5,521,373; which are incorporated by reference as if fully set forth herein. An additional example is the COMPTON detector (http://www.ucl.ac.uk/MedPhys/posters/giulia/giulia.htm). FIG. 8 shows a scan optionally made by spatially sensitive radioactive emission detector 22" (such as a gamma camera).

Thus, as now afforded by the present invention, connecting a radioactive emission detector to a position tracking system, permits simultaneous radioactivity detecting and position tracking at the same time. This enables the accurate calculation of the shape, size and contour of the radiating object and it's precise position in a three-dimensional space.

The present invention thus provides a method for defining a position of a radioactivity emitting source in a system-of-coordinates. The method is effected by (a) providing a radioactive emission detector which is connected to or communicating with a position tracking system; and (b) monitoring radioactivity emitted from the radioactivity emitting source, while at the same time, monitoring the position of radioactive emission detector in the system-of-coordinates, thereby defining the position of the radioactivity emitting source in the system-of-coordinates.

It will be appreciated by one of skills in the art that the model produced by system 20 is projectable onto any number of other systems-of coordinates, or alternatively, the system-of-coordinates defined by position tracking system 24 may be shared by other position tracking systems, as is further detailed hereinunder, such that no such projection is required.

Thus, as is further shown in FIG. 1, system 20 of the present invention can be used for calculating a position of a radioactivity emitting source in a first system-of-coordinates 28 and further for projecting the position of the radioactivity emitting source onto a second system-of-coordinates 28'. The system includes radioactive emission detector 22, position tracking system 24 which is connected to and/or communicating with radioactive emission detector 22, and data processor 26 which is designed and configured for (i) receiving data inputs from position tracking system and from radioactive emission detector; (ii) calculating the position of the radioactivity emitting source in the first system-of-coordinates; and (iii) projecting the position of the radioactivity emitting source onto the second system-of-coordinates.

A method for calculating a position of a radioactivity emitting source in a first system-of-coordinates and for projecting the position of the radioactivity emitting source onto a second system-of-coordinates is also offered by the present invention. This method is effected by (a) providing a radioactive emission detector being connected to or communicating with a position tracking system; and (b) monitoring radioactivity being emitted from the radioactivity emitting source, while at the same time, monitoring the position of the radioactive emission detector in the first system-of-coordinates, thereby defining the position of the radioactivity emitting source in the first system-of-coordinates and projecting the position of the radioactivity emitting source onto the second system-of-coordinates.

It will be appreciated that the combination of a radioactive emission detector and a position tracking system connected thereto and/or communicating therewith a suitable data processor can be used for generating a two or three dimensional image of the radioactivity emitting source. An algorithm can be used to calculate image intensity based on, for example, a probability function which averages radiation counts and generates an image in which the shorter the time interval between radioactive counts, the brighter the image and vise versa, while compensating when a location is re-scanned. A free hand scanning with a directional detector can be employed for this purpose.

In one embodiment, when scanning a body area with the detector, the detector is made to follow a three dimensional surface which defines the body curvatures and in effect is used also as a position tracking pointer. This information can be used to define the position of the radioactive source with respect to the outer surface of the body, so as to create a three dimensional map of both the radioactive source and the body. This approach can also be undertaken in open surgeries, such as open chest surgeries so as to provide the surgeon in real time with information concerning the functionality of a tissue.

The radioactive emission detector which can be used in context of the present invention can be either a beta emission detector, a gamma emission detector, or a combination of both beta and gamma emission detector. The latter detector can be used to improve localization by sensing for example gamma emission distant from the source and sensing beta or positrons emission closer to the source. A beta detector is dedicated for the detection of either electrons from sources such as $^{131}$Iodine, or positrons from sources such as $^{18}$Fluor. A gamma detector can be designed as a single energy detector or as a detector that can distinguish between different types of energies, this can be achieved, for example, by using scintillation crystals of different width. The latter configuration is useful to closely locate a radiation source such as a beta or positron source, since low energy gamma radiation generated by the COMPTON effect, or stopping radiation effect will be more confined to the vicinity of the radiation source. Also, the detector can be designed to utilize coincidence detection by using detectors facing one another (180 degrees) with the examined organ or tissue in-between. The radiation detector can have different collimators, such as a collimator with multiple slits for high sensitivity lower spatial resolution. When approaching the radiation source it can be switched to a single slit higher resolution, lower sensitivity collimator. A shutter can be placed in front of the detector, so as to achieve a similar effect.

System 20 of the present invention can be used in synergetic concert with other medical devices, such as, but not limited to, any one of a variety of imaging modalities and/or surgical instruments.

Imaging modalities are well known in the art, the main modalities that serve for three-dimensional imaging are a fluoroscope, a computerized tomography scanner, a magnetic resonance imager and an ultrasound imager and an optical camera.

Medical images taken of the human body are typically acquired or displayed in three main orientations (i) coronal orientation: in a cross section (plane), for example, across the shoulders, dividing the body into front and back halves; (ii) sagittal orientation: in a cross section (plane), for example, down the middle, dividing the body into left and right halves; and (iii) axial orientation: in a cross section (plane), perpendicular to the long axis of the body, dividing the body into upper and lower halves. Oblique views can also be acquired and displayed.

Various types of X-Ray imaging are central to diagnosis of many types of cancer. Conventional x-ray imaging has evolved over the past 100 years, but the basic principal is still the same as in 1895. An x-ray source is turned on and x-rays are radiated through the body part of interest and onto a film cassette positioned under or behind the body part. The energy and wavelength of the x-rays allows them to pass through the body part and create the image of the internal structures like bones of the hand. As the x-rays pass through the hand, for instance, they are attenuated by the different density tissues they encounter. Bone attenuates a great deal more of the x-rays than the soft tissue around it because of its grater density. It is these differences in absorption and the corresponding varying exposure level of the film that creates the images.

Fluoroscopy is a method based on the principals of film x-ray that is useful for detecting disorders and tumors in the upper gastro-intestinal (GI) system (for example, the stomach and intestines). Fluoroscopic imaging yields a moving x-ray picture. The doctor can watch the screen and see a dynamic image of the patient's body (for example the beating heart). Fluoroscopic technology improved greatly with the addition of television cameras and fluoroscopic "image intensifiers". Today, many conventional X-ray systems have the ability to switch back and forth between the radiographic and fluoroscopic modes. The latest x-ray systems have the ability to acquire the radiograph or fluoroscopic movie using digital acquisition.

Computed Tomography (CT) is based on the x-ray principal, where the film is replaced by a detector that measures the x-ray profile. Inside the covers of the CT scanner is a rotating frame which has an x-ray tube mounted on one side and the detector mounted on the opposite side. A fan beam of x-ray is created as the rotating frame spins the x-ray tube and detector around the patient. Each time the x-ray tube and detector make a 360° rotation, an image or "slice" has been acquired. This "slice" is collimated to a thickness between 1 mm and 10 mm using lead shutters in front of the x-ray tube and x-ray detector.

As the x-ray tube and detector make this 360° rotation, the detector takes numerous profiles of the attenuated x-ray beam. Typically, in one 360° lap, about 1,000 profiles are sampled. Each profile is subdivided spatially by the detectors and fed into about 700 individual channels. Each profile is then backwards reconstructed (or "back projected") by a dedicated computer into a two-dimensional image of the "slice" that was scanned.

The CT gantry and table have multiple microprocessors that control the rotation of the gantry, movement of the table (up/down and in/out), tilting of the gantry for angled images, and other functions such as turning the x-ray beam on an off. The CT contains a slip ring that allows electric power to be transferred from a stationary power source onto the continuously rotating gantry. The innovation of the power slip ring has created a renaissance in CT called spiral or helical scanning. These spiral CT scanners can now image entire anatomic regions like the lungs in a quick 20 to 30 second breath hold. Instead of acquiring a stack of individual slices which may be misaligned due to slight patient motion or breathing (and lung/abdomen motion) in between each slice acquisition, spiral CT acquires a volume of data with the patient anatomy all in one position. This volume data set can then be computer-reconstructed to provide three-dimensional pictures such as of complex blood vessels like the renal arteries or aorta. Spiral CT allows the acquisition of CT data that is perfectly suited to three-dimensional reconstruction.

MR Imaging is superior to CT in detecting soft tissue lesions such as tumors as it has excellent contrast resolution, meaning it can show subtle soft-tissue changes with exceptional clarity. Thus, MR is often the method of choice for diagnosing tumors and for searching for metastases. MR uses magnetic energy and radio waves to create cross-sectional images or "slices" of the human body. The main component of most MR systems is a large tube shaped or cylindrical magnet. Also, there are MR systems with a C-shaped magnet or other type of open design. The strength of the MR systems magnetic field is measured in metric units called "Tesla". Most of the cylindrical magnets have a strength between 0.5 and 1.5 Tesla and most of the open or C-shaped magnets have a magnetic strength between 0.01 and 0.35 Tesla.

Inside the MR system a magnetic field is created. Each total MR examination typically is comprised of a series of 2 to 6 sequences. An "MR sequence" is an acquisition of data that yields a specific image orientation and a specific type of image appearance or "contrast". During the examination, a radio signal is turned on and off, and subsequently the energy which is absorbed by different atoms in the body is echoed or reflected back out of the body. These echoes are continuously measured by "gradient coils" that are switched on and off to measure the MR signal reflecting back. In the rotating frame of reference, the net magnetization vector rotate from a longitudinal position a distance proportional to the time length of the radio frequency pulse. After a certain length of time, the net magnetization vector rotates 90 degrees and lies in the transverse or x-y plane. It is in this position that the net magnetization can be detected on MRI. The angle that the net magnetization vector rotates is commonly called the 'flip' or 'tip' angle. At angles greater than or less than 90 degrees there will still be a small component of the magnetization that will be in the x-y plane, and therefore be detected. Radio frequency coils are the "antenna" of the MRI system that broadcasts the RF signal to the patient and/or receives the return signal. RF coils can be receive-only, in which case the body coil is used as a transmitter; or transmit and receive (transceiver). Surface coils are the simplest design of coil. They are simply a loop of wire, either circular or rectangular, that is placed over the region of interest.

A digital computer reconstructs these echoes into images of the body. A benefit of MRI is that it can easily acquire direct views of the body in almost any orientation, while CT scanners typically acquire images perpendicular to the long body axis.

Ultrasound imaging is a versatile scanning technique that uses sound waves to create images of organs or anatomical structures in order to make a diagnosis. The ultrasound process involves placing a small device called a transducer, against the skin of the patient near the region of interest, for example, against the back to image the kidneys. The ultrasound transducer combines functions of emitting and receiving sound. This transducer produces a stream of inaudible, high frequency sound waves which penetrate into the body and echo off the organs inside. The transducer detects sound waves as they echo back from the internal structures and contours of the organs. Different tissues reflect these sound waves differently, causing a signature which can be measured and transformed into an image. These waves are received by the ultrasound machine and turned into live pictures with the use of computers and reconstruction software.

Ultrasound scanning has many uses, including: diagnosis of disease and structural abnormalities, helping to conduct other diagnostic procedures, such as needle biopsies etc.

There are limitations to some ultrasound techniques: good images may not be obtained in every case, and the scan may not produce as precise results as some other diagnostic imaging procedures. In addition, scan results may be affected by physical abnormalities, chronic disease, excessive movement, or incorrect transducer placement.

In many cases imaging modalities either inherently include (e.g., fluoroscope, CT, MRI) and/or are integrated with position-tracking-systems, which enable the use of such systems to reconstruct three-dimensional image models and provide their position in a three-dimensional space.

It will be appreciated that, similar to the vision system, also an optical camera can be used to generate three-dimensional imagery date according to the present invention by imaging a body from a plurality (at least two) directions. This type of imaging is especially applicable in open chest surgeries or other open surgeries. Software for calculating a three dimensional image from a pair of stereoscopic images is well known in the art.

Thus, as used herein and in the claims section that follows, the phrase "three-dimensional imaging modality" refers to any type of imaging equipment which includes software and hardware for generating a three dimensional image. Such an equipment can generate a three dimensional image by imaging successive cross-sections of a body, e.g., as if viewed from a single direction. Alternatively, such an equipment can generate a three dimensional image by imaging a body from different angles or directions (typically two angles) and thereafter combining the data into a three dimensional image.

Surgical instruments are also well known in the art and may use any one of a plurality of configurations in order to perform minimal-invasive surgical procedures. Examples include laser probes, cardiac and angioplastic catheters, endoscopic probes, biopsy needles, aspiration tubes or needles, resecting devices, ultrasonic probes, fiber optic scopes, laparoscopy probes, thermal probes and suction/irrigation probes. Examples of such surgical instruments employed in a variety of contexts are disclosed in, for example, U.S. Pat. Nos. 6,083,170; 6,063,022; 5,954,665; 5,840,025; 5,718,241; 5,713,946; 5,694,945; 5,568,809; 5,546,951; 5,480,422 5,391,199; 5,800,414; 5,843,017; 6,086,554; 5,766,234; 5,868,739; 5,911,719; 5,993,408; 6,007,497; 6,021,341; 6,066,151; 6,071,281; 6,083,166 and 5,746,738, which are incorporated by reference as if fully set forth herein.

For some applications, examples of which are provided in the list of patents above, surgical instruments are integrated with position-tracking-systems, which enable to monitor the position of such instruments while placed in and guided through the body of a treated patient.

According to a preferred embodiment of the present invention the surgical instrument is equipped with an additional radioactive emission detector attached thereto or integrated therein. This additional detector is used, according to preferred embodiments of the invention, to fine tune the location of radioactive emission from within the body, and in closer proximity to the radiative source. Since the surgical tool is preferably connected to or communicating with a position-tracking system, the position of the additional detector can be monitored and its readouts used to fine tune the position of the radiative source. Thus, according to this aspect of the present invention, at least one extracorporeal detector and an intracorporeal detector are used in concert to determine the position of a radiative source in the body in highest precision. The extracorporeal detector provides the general position of the source and is used for directing the surgical instrument thereto, whereas the intracorporeal detector is used for reassuring prior to application of treatment that indeed the source was correctly targeted and for more determining the position of the source in the highest precision.

While according to a presently preferred embodiment of the invention two detectors, one extracorporeal and one intracorporeal, are employed as described above, for some applications a single intracorporeal detector may be employed, which detector is attached to or integrated with a surgical instrument whose position is tracked.

The use of intracorporeal and extracorporeal detectors call for careful choice of the radiative isotope employed in the radiopharmaceutical. While the extracorporeal detector can be constructed with a suitable collimator for handling strong radiation, such as gamma radiation, the intracorporeal detector is miniature by nature and is limited in design and construction by the construction of the surgical instrument with which it is employed. Since collimators for gamma radiation are robust in nature, they are not readily engagable with miniature detectors. Electron (beta) and positron radiation are characterized by (i) they highly absorbed by biological tissue as they are of lower energy and chemical reactivity; and (ii) they are readily collimated and focused by thin metal collimators. As such, the radio pharmaceutical of choice is selected to emit both gamma and beta and/or positron radiation, whereas the extracorporeal detector is set to detect the gamma radiation, whereas the intracorporeal detector is set to detect the beta and/or positron radiation. Isotopes that emit both gamma and beta and/or positron radiation and which can be used per se or as a part of a compound as radiopharmaceuticals include, without limitation, $^{18}$F, $^{111}$In and $^{123}$I in radiopharmaceuticals, such as, but not limited to, 2-[$^{18}$F]fluoro-2-deoxy-D-glucose ($^{18}$FDG), $^{111}$In-Pentetreotide ([$^{111}$In-DTPA-D-Phe$^1$]-octreotide), L-3-[$^{123}$I]-Iodo-alpha-methyl-tyrosine (IMT), O-(2-[$^{18}$F]fluoroethyl)-L-tyrosine (L-[$^{18}$F] FET), $^{111}$In-Capromab Pendetide (CYT-356, Prostascint) and $^{111}$In-Satumomab Pendetide (Oncoscint).

Figure 11:
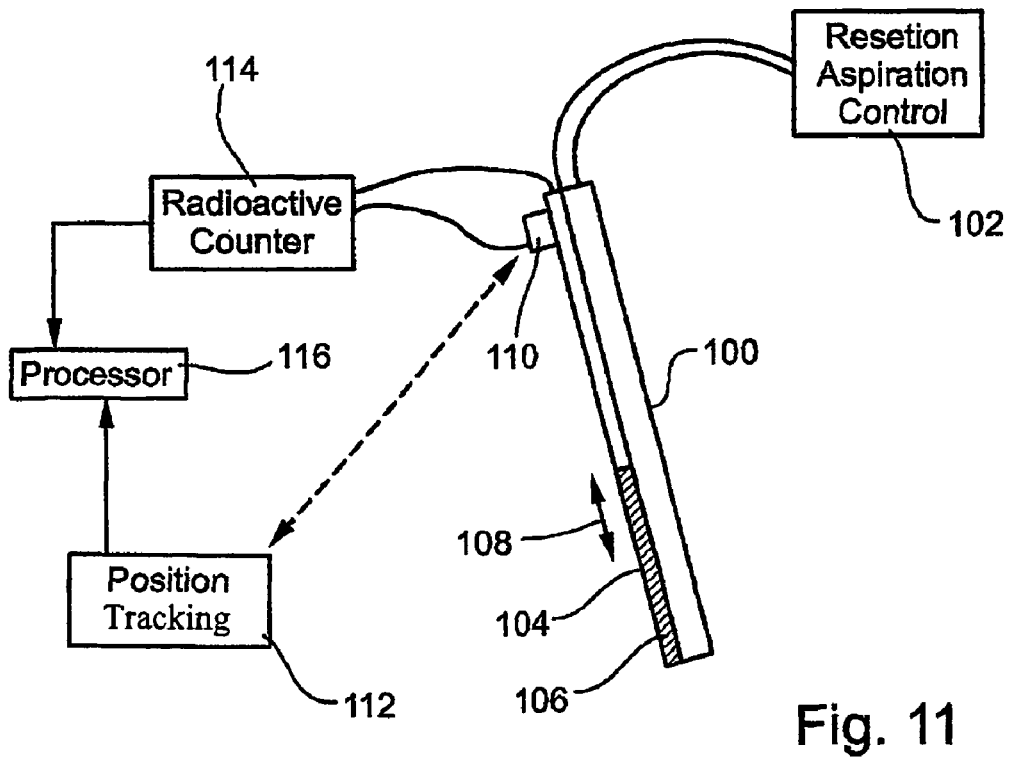
FIG. 11 is a schematic diagram of a surgical instrument and accompanying system elements according to the teachings of the present invention.

FIG. 11 illustrates a system in accordance with this aspect of the present invention. A surgical instrument 100 is shown connected to a resection/aspiration control element 102 as well known in the art. Surgical instrument 100 includes a radioactive emission detector 104, which has a collimator 106 for collimating beta or positron radiation. In some embodiments, as indicated by arrow 108, detector 104 may be translated within instrument 100. A position tracking system having one element thereof 110 attached to instrument 100 and another element thereof 112 at a fixed location serve to monitor the position of instrument 100 at all times in six degrees of freedom. Radioactive emission detector 104 communicates with a counter 114 for counting beta or positron radiation. All the data is communicated to and processed by a processor 116. The 3D data may be projected and displayed along with 3D imaging data derived from an imaging modality using a shared presentation device as described elsewhere herein. A virtual image of the surgical instrument itself may also be co-displayed. Examples commercial radiation emission detectors that can fit inside, for example, a biopsy needle include scintillating plastic optical fibers like S101 and S104, manufactured by PPLASTIFO or an optical fiber communicating with a scintillatior (either detector paint or scintillation crystal) at the fiber edge. Level of radiation can be reported visually or by an audio signal, as is well known in the art.

Thus, a surgical instrument equipped with a radiation emission detector and which is connected to and/or communicating with a position tracking system forms one embodiment of this aspect of the present invention. Such a design acting in concert with either conventional imaging modalities and/or extracorporeal radiation emission detectors form other embodiments of this aspect of the invention. In all cases, a surgical instrument equipped with a radiation emission detector and which is connected to and/or communicating with a position tracking system serves for in situ fine tuning of a radioactive source in the body.

It will be appreciated that in some minimally-invasive procedures even the position of the patient him or herself is monitored via a position tracking system, using, for example, electronic feducial markers attached at certain locations to the patient's body.

Thus, as is further detailed hereinunder, by projecting the three-dimensional data and positions received from any of the above mentioned devices into a common system of coordinates, or alternatively, employing a common position tracking system for all of these devices, one can integrate the data into a far superior and comprehensive presentation.

Figure 9:
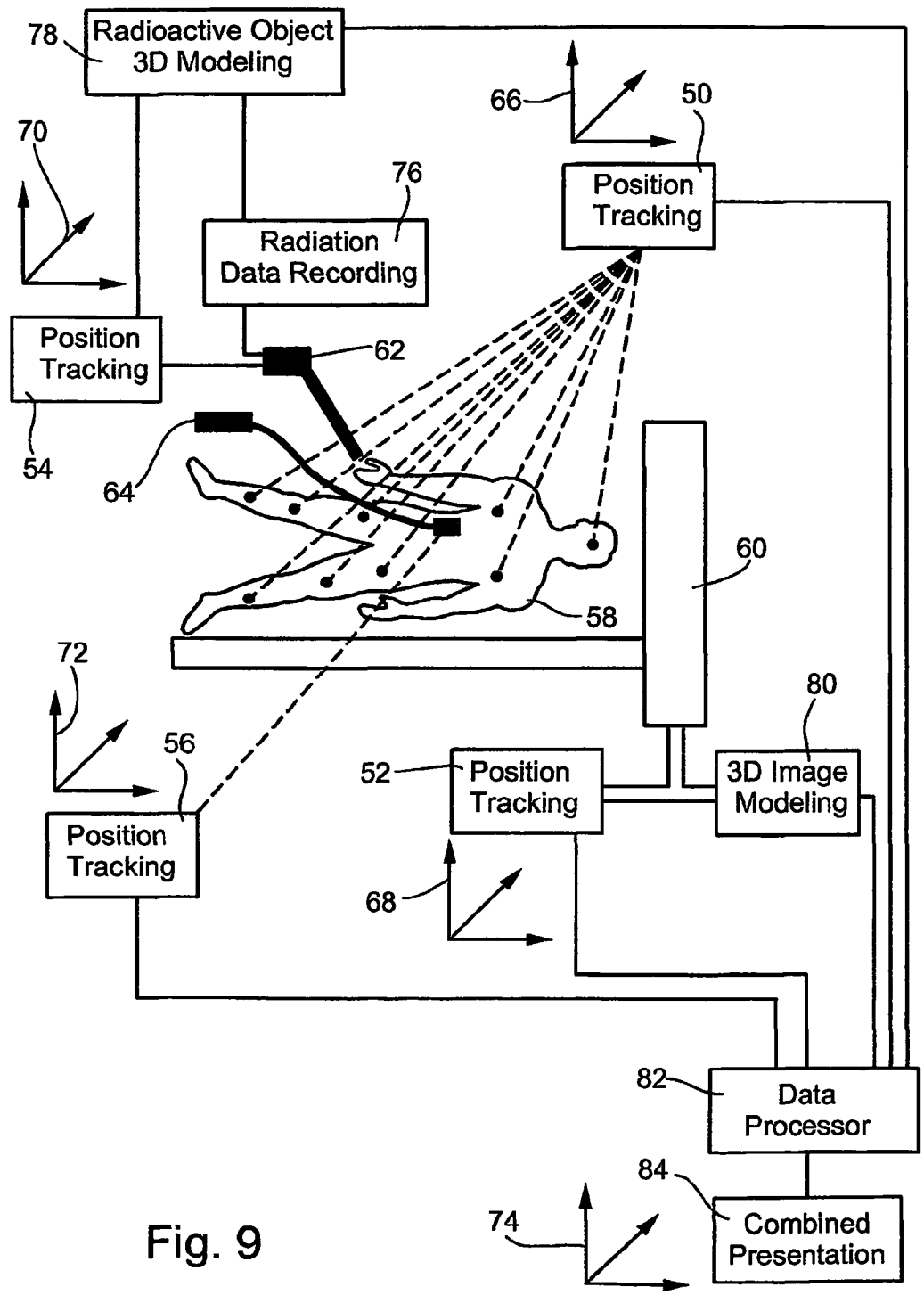
FIG. 9 demonstrates a system in accordance with the teachings of the present invention which employs four position tracking systems for co-tracking the positions of a patient, a radioactive emission detector, an imaging modality and a surgical instrument.

An example to this effect is shown in FIG. 9. In the embodiment shown, four independent position tracking systems 50, 52, 54 and 56 are used to track the positions of a patient 58, an imaging modality 60, a radioactive emission detector 62 and a surgical instrument 64 in four independent systems-of-coordinates 66, 68, 70 and 72, respectively. If the patient is steel, no tracking of the patient's position is required.

It will be appreciated that any subset or all of the position tracking systems employed may be integrated into one or more common position tracking systems, and/or that any subset or all of the position tracking systems employed may share one or more systems-of-coordinates, and further that any positional data obtained by any of the position tracking systems described in any of the systems-of coordinates may be projected to any other system of coordinates or to an independent (fifth) system of coordinates 74. In one preferred embodiment, applicable for applications at the torso of the patient, the system of coordinates is a dynamic system of coordinates which takes into account the chest breathing movements of the patient during the procedure.

As indicated at 76, the radioactive data collected by detector 62 is recorded and, as indicated at 78, the position and the radioactive data records are used to generate a three-dimensional model of a radiopharmaceutical uptaking portion of a body component of the patient.

Similarly, as indicated at 80, the imagery data collected by imaging modality 60 is recorded and the position and the imagery data records are used to generate a three-dimensional model of the imaged body component of the patient.

All the data collected is then fed into a data processor 82 which processes the data and, as indicated at 84, generates a combined or superimposed presentation of the radioactive data and the imagery data, which is in positional context with patient 58 and surgical instrument 64.

Instrument 64, which by itself can be presented in context of the combined presentation, may then be used to perform the procedure most accurately. Processor 82 may be a single entity or may include a plurality of data processing stations which directly communicate with, or even integral to, any one or more of the devices described.

The present invention provides a major advantage over prior art designs because it positionally integrates data pertaining to a body portion as retrieved by two independent imaging techniques, conventional imaging and radioactive imaging, to thereby provide a surgeon with the ability the fine point the portion of the body to be sampled or treated.

It will be appreciated that subsets of the devices described in FIG. 9 may be used as stand-alone systems. For example, a combination of detector 62 with its position-tracking system and instrument 64 with its position-tracking-system may in some instances be sufficient to perform intrabody procedures. For mere diagnostic purposes a combination of detector 62 position-tracking-system and modality 60 position-tracking-system are sufficient.

The following provides a list of known procedures which can take advantage of the system and method of the present invention:

In cancer diagnosis the system and method of the present invention can find uses for screening for cancer and/or directing invasive diagnosis (biopsies) either from outside the body or by way of endoscopic approach. Examples include, but are not limited to, lung cancer biopsy, breast cancer biopsy, prostate cancer biopsy, cervical cancer biopsy, liver cancer biopsy, lymph node cancer biopsy, thyroid cancer biopsy, brain cancer biopsy, bone cancer biopsy, colon cancer biopsy, gastro intestine cancer endoscopy and biopsy, endoscopic screening for vaginal cancer, endoscopic screening for prostate cancer (by way of the rectum), endoscopic screening for ovarian cancer. (by way of the vagina), endoscopic screening for cervical cancer (by way of the vagina), endoscopic screening for bladder cancer (by way of the urinary track), endoscopic screening for bile cancer (by way of the gastrointestinal track), screening for lung cancer, screening for breast cancer, screening for melanoma, screening for brain cancer, screening for lymph cancer, screening for kidney cancer, screening for gastro intestinal cancer (from the outside).

Procedures known as directing localized treatment of cancer can also benefit from the system and method of the present invention. Examples include, but are not limited to, intra tumoral chemotherapy, intra tumoral brachytherapy, intra tumoral cryogenic ablation, intra tumoral radio frequency ablation, intra tumoral ultrasound ablation, and intra tumoral laser ablation, in cases of, for example, lung cancer, breast cancer, prostate cancer, cervical cancer, liver cancer, lymph cancer, thyroid cancer, brain cancer, bone cancer, colon cancer (by way of endoscopy through the rectum), gastric cancer (by way of endoscopy through the thorax), thoracic cancer, small intestine cancer (by way of endoscopy through the rectum or, by way of endoscopy through the thorax), bladder cancer, kidney cancer, vaginal cancer and ovarian cancer.

In interventional cardiology the following procedures can take advantage of the present invention wherein the method and system can be used to assess tissue perfusion, tissue viability and blood flow intra operatively during PTCA procedure (balloon alone or in conjunction with the placement of a stent), in cases of cardiogenic shock to asses damage to the heart, following myocardial infarct to asses damage to the heart, in assessing heart failure condition tissue in terms of tissue viability and tissue perfusion, in intra vascular tissue viability and perfusion assessment prior to CABG operation.

Using the method and system of the present invention to assess tissue perfusion, tissue viability and blood flow intra operatively can also be employed in the following: during CABG operation to asses tissue viability, to mark infarct areas, during CABG operations to asses the success of the re vascularization.

It will be appreciated that many other procedures may also take advantage of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for radioactive emission imaging after an administration of a radiopharmaceutical, by calculating a position of a radioactivity emitting source in an overall system-of-coordinates, the system comprising:
   (a) a first radioactive emission detector;
   (b) a first position tracking system, associated with said first radioactive emission detector, and operative in a first system-of-coordinates;
   (c) at least a second radioactive emission detector, physically connected to said first radioactive emission detector, by a flexible connection;
   (d) at least a second position tracking system, associated with said at least second radioactive emission detector, and operative in at least a second system-of-coordinates;
   (e) a data processor programmed to receive data inputs from said position tracking systems and from said radioactive emission detectors and to calculate the position of the radioactivity emitting source in the overall system-of-coordinates,
   wherein said first and at least second radioactive emission detectors are configured for scanning a three dimensional surface which define body curvatures, while following contours of said three dimensional surface,
   and wherein said flexible connection constrains said first and second radioactive emission detectors while said detectors follow contours of said three dimensional surface, to point towards the vicinity of said radioactivity emitting source.

2. The system of claim 1, wherein the radioactivity emitting source is selected from the group consisting of a radiopharmaceutically labeled benign tumor, a radiopharmaceutically labeled malignant tumor, a radiopharmaceutically labeled vascular clot, radiopharmaceutically labeled inflammation related components, a radiopharmaceutically labeled abscess and a radiopharmaceutically labeled vascular abnormality.

3. The system of claim 1, wherein each of said radioactive emission detectors is selected from the group consisting of a narrow beam radioactive emission detector and a spatially sensitive radioactivity detector.

4. The system of claim 1, wherein each of said position tracking systems is selected from the group consisting of an articulated arm position tracking system, an accelerometers based position tracking system, a potentiometers based position tracking system, a sound wave based position tracking system, a radiofrequency based position tracking system, an electromagnetic field based position tracking system and an optical based position tracking system.

5. The system of claim 1, and further comprising at least one other three-dimensional imaging modality, different from radioactive emission imaging, the at least one other three-dimensional imaging modality being associated with an at-least-one-other-imaging-modality position tracking system, operative in an at-least-one-other-imaging-modality system-of-coordinates, for calculating the position of a body component in the at-least-one-other-imaging-modality system-of-coordinates,
   wherein the data processor is further designed and configured for receiving data inputs from said three-dimensional imaging modality, and said at-least-one-otherimaging-modality position tracking system, and calculating the position of the body component and the position of the radioactivity emitting source in the overall system-of-coordinates.

6. The system of claim 5, wherein said at least one other imaging modality communicates with an image presentation device which serves for visual co-presentation of said body component and said radioactivity emitting source.

7. The system of claim 5, wherein said imaging modality is selected from the group consisting of a Fluoroscope, a Computed Tomographer, an Magnetic Resonance Imager, an ultrasound imager and an optical camera.

8. The system of claim 1, wherein said radiopharmaceutical is selected from the group consisting of .sup.137I, .sup.67Ga, .sup.99MTc methoxyisobutyl isonitrile, .sup.201TlCl, .sup.18F-fluorodeoxyglucose, .sup.125I-fibrinogen and .sup.111In-octreotide.

9. The system of claim 1, and further comprising:
a surgical instrument associated with a surgical-instrument position tracking system, operative in a surgical-instrument system-of-coordinates, for tracking a position of said surgical instrument in a surgical-instrument system-of-coordinates;
wherein said data processor is further designed and configured for receiving data inputs from said surgical-instrument position tracking system and for calculating the position of the surgical instrument and the radioactivity emitting source in the overall system-of-coordinates.

10. The system of claim 9, wherein said surgical instrument includes an additional radioactive emission detector, whereas said at least one data processor is further designed and configured for receiving data inputs from said additional radioactive emission detector for refining the position of the radioactivity emitting source in the overall system-of-coordinates.

11. The system of claim 9, further comprising an image presentation device which serves for visual co-presentation of the position of said surgical instrument and the radioactivity emitting source.

12. The system of claim 9, wherein said surgical instrument is selected from the group consisting of laser probe, cardiac catheter, angioplastic catheter, endoscopic probe, biopsy needle, ultrasonic probe, fiber optic scopes, aspiration tubes, laparoscopy probe, thermal probe, suction/irrigation probe and pointing device.

13. The system of claim 1, wherein said radiopharmaceutical is selected from the group consisting of 2-[.sup.18F] fluoro-2-deoxy-D-glucose, .sup.111In-Pentetreotide, L-3-[.sup.123I]-Iodo-alpha-methyl-tyrosine, O-(2-[.sup.18F] fluoroethyl)-L-tyro sine, .sup.111In-Capromab Pendetide and .sup.111In-Satumomab Pendetide.

14. The system of claim 1, wherein said flexible connector is selected from the group consisting of a cable, a hinge, an articulated system of arms and joints, and a combination thereof.

15. The system of claim 1, wherein said three dimensional surface is defined by body curvatures of a living body that is scanned.

16. The system of claim 1, wherein said three dimensional surface is defined by extracorporeal body curvatures of a living body that is scanned.

17. The system of claim 1, wherein said three dimensional surface is defined by a body lumen of a living body that is scanned.

18. The system of claim 1, wherein said three dimensional surface is defined by body curvatures of a living body that is scanned, during surgery.

19. The system of claim 1, configured for providing real time information concerning the functionality of a tissue.

20. The system of claim 1, wherein said flexible connector is selected from the group consisting of a cable, a hinge, a system of arms and hinges, and a combination thereof.

21. The system of claim 1 wherein said first radioactive emission detector is mounted on an arm and said first position tracking system is integrated into said arm.

22. The system of claim 1, wherein said first and at least second radioactive emission detectors are configured for scanning a three dimensional surface which define body curvatures, while positioned on the same side of said three dimensional surface.

23. A method for radioactive emission imaging after an administration of a radiopharmaceutical, by defining a position of a radioactivity emitting source in an overall system-of-coordinates, the method comprising the steps of:
(a) providing: (i) a first radioactive emission detector;
(ii) a first position tracking system, associated with said first radioactive emission detector, and operative in a first system-of-coordinates;
(iii) at least a second radioactive emission detector, physically connected to said first radioactive emission detector, by a flexible connection;
(iv) at least a second position tracking system, associated with said at least second radioactive emission detector, and operative in at least a second system-of-coordinates;
(v) a data processor, programmed to receive data inputs from said position tracking systems and from said radioactive emission detectors and to calculate the position of the radioactivity emitting source in the overall system-of-coordinates;
(b) employing said radioactive emission detectors, while constraining said radioactive emission detectors to point towards the vicinity of said radioactivity emitting source, in scanning a three dimensional surface which define body curvatures, while following contours of said three dimensional surface; and
(c) monitoring radioactivity being emitted from the radioactivity emitting source, while at the same time, monitoring the position of each of said radioactive emission detectors in the overall system-of-coordinates, thereby defining the position of the radioactivity emitting source in the overall system-of-coordinates.

24. The method for claim 23, wherein the radioactivity emitting source is selected from the group consisting of a radiopharmaceutically labeled benign tumor, a radiopharmaceutically labeled malignant tumor, a radiopharmaceutically labeled vascular clot, radiopharmaceutically labeled inflammation related components, a radiopharmaceutically labeled abscess and a radiopharmaceutically labeled vascular abnormality.

25. The method for claim 23, wherein each of said radioactive emission detectors is selected from the group consisting of a narrow beam radioactive emission detector and a spatially sensitive radioactivity detector.

26. The method for claim 23, wherein each of said position tracking systems is selected from the group consisting of an articulated arm position tracking system, an accelerometers based position tracking system, a potentiometers based position tracking system, a sound wave based position tracking system, a radiofrequency based position tracking system, an electromagnetic field based position tracking system and an optical based position tracking system.

27. The method of claim 23, and further comprising:
providing at least one other three-dimensional imaging modality, different from radioactive emission imaging, the at least one other three-dimensional imaging modality being associated with an at-least-one-other-imaging-modality position tracking system, operative in an at-least-one-other-imaging-modality system-of-coordinates, for calculating the position of the body component in the at-least-one-other-imaging-modality system-of-coordinates;
receiving data inputs from said at least one other three-dimensional imaging modality, and said at-least-one-other-imaging-modality position tracking system; and
calculating the position of the body component and the position of the radioactivity emitting source in the overall system-of-coordinates.

28. The method for claim 27, wherein said at least one other imaging modality communicates with an image presentation device which serves for visual co-presentation of said body component and said radioactivity emitting source.

29. The method for claim 27, wherein said imaging modality is selected from the group consisting of a fluoroscope, a computerized tomography scanner, a magnetic resonance imager and an ultrasound imager and an optical camera.

30. The method for claim 23, wherein said radiopharmaceutical is selected from the group consisting of $^{137}$I, $^{67}$Ga, $^{99m}$Tc methoxyisobutyl isonitrile, $^{201}$TlCl, $^{18}$F-fluorodeoxyglucose, $^{125}$I-fibrinogen and $^{111}$In-octreotide.

31. The method of claim 23, and further comprising:
providing a surgical instrument, associated with a surgical-instrument position tracking system, operative in a surgical instrument syste-of-cooridinates;
tracking a position of said surgical instrument in the surgical instrument system-of-coordinates, while performing the intrabody surgical procedure;
receiving data inputs from the surgical-instrument position tracking system; and
calculating the position of the surgical instrument and the radioactivity emitting source in an overall system-of-coordinates, while performing the intrabody surgical procedure.

32. The method of claim 31, wherein said surgical instrument includes an additional radioactive emission detector, whereas said data processor is further designed and configured for receiving data inputs from said additional radioactive emission detector for refining the position of the radioactivity emitting source in the overall system-of-coordinates.

33. The method for claim 31, wherein said surgical instrument is selected from the group consisting of laser probe, cardiac catheter, angioplastic catheter, endoscopic probe, biopsy needle, ultrasonic probe, fiber optic scopes, aspiration tubes, laparoscopy probe, thermal probe and suction/irrigation probe.

34. The method for claim 31, further comprising the step of co-presenting the position of said surgical instrument and the radioactivity emitting source via a visual presentation device.

35. The method for claim 23, wherein said radiopharmaceutical is selected from the group consisting of 2-[$^{18}$F]fluoro-2-deoxy-D-glucos-e, $^{111}$In-Pentetreotide, L-3-[$^{123}$I]-Iodo-alpha-methyl-tyrosine, O-(2-[18F]fluoroethyl)-L-tyrosine, $^{111}$In-Capromab Pendetide and $^{111}$In-Satumomab Pendetide.

36. The method of claim 23, wherein said flexible connector is selected from the group consisting of a cable, a hinge, an articulated system of arms and joints, and a combination thereof.

37. The method of claim 23, wherein said three dimensional surface is defined by body curvatures of a living body that is scanned.

38. The method of claim 23, wherein said three dimensional surface is defined by extracorporeal body curvatures of a living body that is scanned.

39. The method of claim 23, wherein said three dimensional surface is defined by a body lumen of a living body that is scanned.

40. The method of claim 23, wherein said three dimensional surface is defined by body curvatures of a living body that is scanned, during surgery.

41. The method of claim 23, configured for providing real time information concerning the functionality of a tissue.

42. The method of claim 23, wherein said flexible connector is selected from the group consisting of a cable, a hinge, a system of arms and hinges, and a combination thereof.

43. The method of claim 23, wherein scanning a three dimensional surface which define body curvatures, while following contours of said three dimensional surface comprises scanning while the detectors are positioned at the same side of said three dimensional surface.

* * * * *